United States Patent [19]

Hamada et al.

[11] Patent Number: 4,738,926

[45] Date of Patent: Apr. 19, 1988

[54] METHOD FOR PURIFICATION OF HBS ANTIGEN

[75] Inventors: Fukusaburo Hamada, Nishigoshi; Keishin Sugahara, Kumamoto; Kou-ichi Shiosaki, Kumamoto; Satoshi Adachi, Kumamoto; Hiroshi Mizokami, Kikuchi, all of Japan

[73] Assignee: Juridical Foundation The Chemo-Sero-Therapeutic Research Institute, Kumamoto, Japan

[21] Appl. No.: 709,711

[22] Filed: Mar. 8, 1985

[30] Foreign Application Priority Data

Mar. 16, 1984 [JP] Japan .................. 59-51654

[51] Int. Cl.$^4$ .............................. C12N 7/02
[52] U.S. Cl. ........................ 435/239; 435/5; 435/68; 435/174; 435/176; 435/235; 435/803; 435/820; 436/161; 436/543; 530/417; 530/826
[58] Field of Search ............ 435/5, 174, 176, 235, 435/239, 803, 820, 68; 436/161, 543; 530/417, 826

[56] References Cited

U.S. PATENT DOCUMENTS

| | | | |
|---|---|---|---|
| 3,951,937 | 4/1976 | Vnek et al. | 435/239 |
| 4,071,619 | 1/1978 | Peradze et al. | 435/239 |
| 4,102,996 | 7/1978 | McAleer et al. | 435/239 |

OTHER PUBLICATIONS

R. A. Hitzeman et al., Nucleic Acid Research, vol. 11, No. 9, pp. 2745–2763, (1983).
Valenzuela et al., Nature, vol. 298, pp. 347–350, (1982).
Miyanohara et al., Proc. Natl. Acad. Sci., USA, vol. 80, pp. 1–5, (1983).

*Primary Examiner*—Esther M. Kepplinger
*Assistant Examiner*—Stephen C. Wieder
*Attorney, Agent, or Firm*—Wegner & Bretschneider

[57] ABSTRACT

Industrially useful method for the purification of HBs antigen produced by a recombinant organism being capable of producing HBs antigen which is prepared by means of DNA recombination technique, which comprises subjecting an HBs antigen-containing material produced by a recombinant organism to an adsorption chromatography with a silica, optionally followed by a gel filtration and further an adsorption chromatography with a hydroxyapatite, and then eluting the HBs antigen, preferably, with a buffer having a pH 9 or more which is incorporated with urea. The purification method can give a highly pure HBs antigen suitable for the preparation of hepatitis B vaccine in a large scale from recombinant organisms prepared by DNA recombination technique.

3 Claims, No Drawings

METHOD FOR PURIFICATION OF HBS ANTIGEN

The present invention relates to a method for the purification of hepatitis B virus surface antigen (hereinafter referred to as "HBs antigen"). More particularly, it relates to an industrially useful method for the purification of HBs antigen produced by recombinant organisms by means of DNA recombination technique.

TECHNICAL BACKGROUND AND TECHNICAL FIELD

Hepatitis B is a disease which is induced by a hepatitis B virus (hereinafter, referred to as "HBV") and includes immunologically and clinically very serious problems, but there has never been found any effective therapeutic method therefor. This disease has been observed worldwidely, particularly in Asia and Africa areas.

Against the disease, prophylactic method has mostly been studied. Suitable prophylaxis is a method of applying a vaccine comprising as an effective ingredient HBs antigen to persons who are afraid to be infected by HBV. A vaccine has already been in practical use, which is prepared by highly purifying an HBs antigen obtained from a blood plasma of latent virus carriers who are usually called as merely "carrier", and inactivating the purified HBs antigen.

However, the blood-origin vaccine is obtained from blood plasma of HBs antigen-positive persons, and hence, it has various problems for the preparation thereof, such as necessity of safety test in chimpanzee in order to prove no remaining of infectious factors such as HBV or any other blood-origin viruses in the preparation; and difficulty to get sufficient chimpanzees for the test.

In order to eliminate such problems, many researchers have been studied on technique for obtaining a large amount of the HBs antigen by introducing an HBV DNA encoding the HBs antigen protein into *Escherichia coli* or an yeast by means of a DNA recombination technique and then expressing the HBs antigen by the transformant microorganisms thus obtained. Recently, the expression of HBs antigen with these recombinant organisms has been succeeded. Particularly, the production of HBs antigen with a recombinant yeast has been accomplished in an industrial scale, and it has been tried to purify the HBs antigen thus obtained and to prepare a hepatitis B vaccine preparation therefrom. In order to use practically the recombinant-origin HBs antigen, there is still a problem that the HBs antigen produced by the recombinant organisms must be highly purified in a so high degree suitable for the desired vaccine stock or for diagnosis.

PRIOR ART

The commonly used purification methods of HBs antigen are a density gradient centrifugation [cf. Vyas, G. N. et al., J. Immunology, 108, 114 (1972)], a combination of a polyethylene glycol fractionation, gel filtration and centrifugation (cf. Japanese Patent Second Publication No. 21246/1982), and a combination of salting out by ammonium sulfate and gel filtration (cf. Japanese Patent First Publication No. 38617/1983). For the purification of HBs antigen obtained from a recombinant organism, there is also proposed a combination of an aqueous polymer two-phase system, ion exchange and gel filtration [cf. Hitzeman, R. A. et al, Nucleic Acid Research, 11, 2745 (1983)]. However, these methods can not still remove the problems in the purification of HBs antigen obtained from a recombinant organism and are hardly used as an industrial purification method.

In case of purification of HBs antigen obtained from a recombinant organism, there are some problems that the components contaminated in the starting materials, such as recombinant-origin proteins, lipids and other components, are essentially different from the contaminants in case of HBs antigen obtained from human blood not only in the kinds but also in the quantity, and that the amount of the contaminants in case of the HBs antigen obtained from a recombinant oganism is far larger than that in case of the HBs antigen obtained from a human blood. Besides, the present inventors have found that it has another problem that the HBs antigen is rapidly inactivated by a substance having a protease activity which is derived from the cells contaminated in the antigen. Accordingly, unless the substance having a protease activity is completely removed from the HBs antigen at an early stage as possible, the yield of the HBs antigen is significantly decreased during the purification step. Moreover, the recombinant-origin HBs antigen has somewhat different affinity (biological affinity) from that of the human blood-origin HBs antigen. This is an additional problem for carrying the purification.

From these viewpoints, the conventional purification methods applicable to the HBs antigen obtained from human blood are not satisfactorily applied for the purification of the recombinant-origin HBs antigen and for overcoming the specific problems involved therein. Even by the method of Hitzeman et al who have tried to purify a recombinant-origin HBs antigen, only a sample for biological analysis is obtained, which is merely purified in such a degree that it can be analyzed, but it can not give such a highly pure product as it can be used as a vaccine or a diagnostic product. They have studied neither on the yield nor the deactivation of HBs antigen by a substance having a protease activity. Thus, such a method can not be used for the purification of a recombinant-origin HBs antigen in an industrial scale.

OBJECT OF THE INVENTION

The present inventors have intensively studied on purification of a recombinant-origin HBs antigen in an industrial scale and have found that when an HBs antigen-containing material which is obtained from a culture medium of a recombinant organism is contacted with silica, the HBs antigen is adsorbed onto the silica but most of the contaminated lipids and proteins origined from the culture cells can be removed without being adsorbed, and when it is followed by elution under specific conditions, the substance having a protease activity adsorbed simultaneously can be selectively eluted out and removed to give an HBs antigen-containing fraction containing no substance having a protease activity, and further that the HBs antigen can greatly highly purified by subjecting it subsequently to a chromatography with hydroxyapatite after the interjacent gel filtration.

An object of the present invention is to provide a purification method of HBs antigen obtained from a recombinant organism by a DNA recombination technique in an industrial scale, in a high efficiency and in a very high purity, which can give an HBs antigen suitable for preparing a stable and effective HBV vaccine. Another object of the invention is to provide an improved method for purification of a recombinant-origin HBs antigen by a chromatography with silica. These and other objects and advantages of the present invention are apparent to persons skilled in the art from the following description.

DETAILED DESCRIPTION OF THE INVENTION

The method for the purification of HBs antigen produced by a recombinant organism utilizing a DNA recombination technique of the present invention comprises subjecting a starting material containing HBs antigen obtained from a culture of a recombinant organism to an adsorption chromatography with silica to give an HBs antigen-containing fraction wherein the most of the contaminants such as lipids and contaminant proteins origined from the host cells are removed, subjecting optionally the fraction to an interjacent gel filtration, and then subjecting the resultant mixture to an affinity chromatography with a hydroxyapatite.

The starting HBs antigen-containing material used in the present invention is usually obtained by a conventional DNA recombination technique, that is, by introducing an HBs antigen coding gene isolated from HBV DNA into a microorganism (e.g. E. coli, or an yeast) or an animal culture cell, by which the microorganism or animal cell is transformed with the gene, and producing HBs antigen by culturing the transformed organism under the action of HBs antigen gene. Such techniques have already been known. For instance, a method of the preparation of a recombinant yeast-origin HBs antigen is reported by Valenzuela (cf. Valenzuela, Nature, 298, 347 (1982) and Japanese Patent First Publication No. 77823/1983), which comprises preparing a shuttle vector (pHBs 16) wherein an HBs gene is bound into a yeast alcohol dehydrogenase promoter in a shuttle vector (pMA 56) having a replication initiating region of pBR 322 plasmid, a replication initiating region of $2\mu$ plasmid, Trp1, and an yeast alcohol dehydrogenase promoter region, introducing the shuttle vector into an yeast to prepare a transformed yeast, and culturing the transformed yeast to produce the desired HBs antigen.

Other known method for preparing an yeast-origin HBs antigen is reported by Miyanohara et al. (cf. Proc. Natl. Acad. Sci., USA, 80, 1 (1983) and Japanese Patent First Publication No. 31799/1984], which comprises preparing a shuttle vector (pAH 203) wherein an HBs gene is bound into a repressible acid phosphatase promoter in a shuttle vector (pAM 82) having a replication initiating region of $2\mu$ plasmid, a replication initiating region of pBR 322 plasmid, a replication initiating region of an yeast chromosome, leu 2 gene of an yeast participating in leucine synthesis, an ampicillin-resistant gene of E. coli, and a region of a repressible acid phosphatase promoter of an yeast, introducing the shuttle vector into an yeast [AH 22 (a, leu2, his4, Canl, Cir+)] to prepare a transformed yeast, and culturing the transformed yeast to produce the desired HBs antigen.

It is also reported by Hitzeman that a shuttle vector wherein an HBs gene is bound into an yeast 3-phosphoglyceric acid kinase (PGK) promoter is prepared and then is used for prepare a transformed yeast which can produce an HBs antigen [cf. Hitzeman, Nucleic Acids Research, 11 (9), 2745 (1983) and Japanese Patent First Publication No. 109427/1983].

It is further reported by Nozaki et al. that a recombinant DNA is prepared by recombining an HBs gene with a vector having a replication initiating region of SV40 DNA inserted into an E. coli plasmid origined from ColI E1, pMB1 or p15A and being deficient in a region of inhibiting replication in mammalian cells, and a transformed mammalian cells are obtained by transforming the mammalian cells, e.g. mouse LTK$^-$ cells, with the recombinant DNA, and then, the transformed cells are cultured to obtain the desired HBs antigen [cf. 30th Japan Virus Association Meeting, Summary, p-1069 (1982) and Japanese Patent First Publication No. 36698/1984]. There are various other reports of producing HBs antigen by animal cells utilizing DNA recombination techniques, e.g. Japanese Patent First Publication Nos. 56685/1983, 995/1983 and 39784/1982.

The HBs antigen-containing solution is obtained by culturing the transformed organisms, such as transformed E. coli or yeasts prepared by a DNA recombination technique in a suitable medium under suitable culture conditions to produce and accumulate HBs antigen in the medium, and extracting roughly the HBs antigen from the culture medium by a conventional method.

Extraction of HBs antigen from the culture medium is carried out by a conventional method, for example, by separating the cells from the culture medium by centrifugation, fracturing the cells in an approriate buffer having a pH 6 to 8 (e.g. 0.14 M sodium chloride-added 0.01 M phosphate buffer, pH 7.2) by a conventional method such as ultrasonic fracture, glass beads fracture, Manton-Gaulin fracture, or enzymatic dissolution of the cell walls, followed by fracturing the resulting spheroplast with a detergent, subjecting the fractured cells to centrifugation at a slow speed to remove the cell wall pieces, and further optionally filtering the mixture with a membrane filter to give an HBs antigen-containing material.

The contact of the HBs antigen-containing solution with silica is carried out by a batch method wherein the starting HBs antigen-containing solution is added to silica, followed by stirring the mixture, or by a column method wherein silica is packed within a column and the starting HBs antigen-containing solution is passed through the column to adsorb the antigen thereon. The batch method is preferred.

The silica used in the present invention include a silicic hydrate of the formula: $SiO_2 \cdot nH_2O$ and silicic anhydride of the formula: $SiO_2$, which are used in the form of fine powder or particles. These silica are commercially available, for example, fine powder silicic anhydride: Mizukasil ® (manufactured by Mizusawa Chemical, Japan), Siloid ® (manufactured by Fuji Devison Co., Japan), silica gel, and so on; silicic anhydride: Aerosil ® (manufactured by Nippon Aerosil, Japan), and the like.

The adsorption by a batch method can be carried out as follows.

A silica is added to an HBs antigen-containing solution, and the mixture is well mixed by shaking or centrifuging at a temperature of 0° to 40° C., preferably 4° to 25° C., by which the HBs antigen is adsorbed onto the silica. The time for adsorption may vary depending on the particle shapes of the silica, but in case of fine powder silica, it is sufficient to mix for 30 minutes to 3 hours. Suitable amount of silica is selected in accordance with the particle shape of silica, the content of HBs antigen and contaminants in the starting HBs antigen-containing solution, but is usually in the range of 1 to 10 W/V %, preferably about 5 W/V %, based on the weight of the starting solution, in case of fine powder silica having a particle size of not more than 10 $\mu$m.

After the adsorption, the mixture is subjected to a separation means such as centrifugation or filtration in order to separate the HBs antigen-adsorbed silica and the supernatant.

The HBs antigen-adsorbed silica thus separated is subjected to the first elution step as follows. A buffer having about pH 5 to 9 (e.g. 0.14 M sodium chloride-added 0.01 M phosphate buffer) is added to the HBs antigen-adsorbed silica in an amount of preferably 20 parts by weight or more based on the weight of the silica. The mixture is shaken or stirred in order to remove the contaminants adhered onto the silica. In this step, the substance having a protease activity adhered onto the silica can almost be removed.

It should be mentioned that removal of the substance having a protease activity is very important for purification of HBs antigen, because the substance significantly inactivate the HBs antigen. For instance, when a crude extract of the starting material which contains the substance having a protease activity is kept at 4° C. or even at −20° C., HBs antigen is almost inactivated within about one week. Besides, under some conditions in the purification step, the protease activity is more promoted, and hence, the HBs antigen is occasionally more quickly inactivated.

After the above first elution step, the mixture is subjected to centrifugation or filtration to separate the solid and liquid phases to recover the HBs antigen-adsorbed silica (as the solid phase). This procedure is preferably repeated twice or three times.

The HBs antigen-adsorbed silica is then subjected to the second elution step in order to elute the HBs antigen from silica. The second elution step has firstly been tried by treating the HBs antigen-adsorbed silica with the following eluent:

(1) a solution of sodium deoxycholate in a borate buffer (pH 8 or more) [e.g. 0.05 M sodium borate-boric acid buffer (pH 9.2)+0.5 % sodium deoxycholate], (2) a buffer having pH 10 or more which is prepared by regulating the pH of a buffer (pH 9 or more) with aqueous ammonia [e.g. 0.05 M sodium borate-boric acid buffer + aqueous ammonia (pH 10.5), or 0.05 M sodium carbonate-sodium hydrogen carbonate buffer + aqueous ammonia (pH 10.2)], (3) a buffer having pH 10 or more [e.g. 0.05 M sodium carbonate-sodium hydrogen carbonate buffer (pH 10.3), or 0.05 M sodium borate-sodium hydrogen carbonate buffer (pH 10.5)].

Among the above eluents, when the eluent (2) or (3) is used for the second elution, the eluted HBs antigen is occasionally denatured partly or coagulates, which result disadvantageously in deterioration of biological and/or physical properties of the HBs antigen. This causes also lowering of recovery rate of HBs antigen in the subsequent step. In this viewpoint, it is very important that the elution is carried out in the presence of deoxycholic acid. However, the present inventors have found that in case of using the eluent (1) containing deoxycholic acid, the HBs antigen can be recovered in a high rate, but on the other hand, it has another problem. That is, the deoxycholic acid must be removed from the eluted HBs antigen in order to use it for a vaccine. The removal of deoxycholic acid is not easy, and further, the presence of deoxycholic acid causes disadvantageously lowering of purification rate in the subsequent procedures. Thus, the presence of deoxycholic acid is not preferable.

From this viewpoint, the present inventors have further studied on the conditions in the second elution step suitable, for eluting effectively HBs antigen without the above disadvantages, and have found that when urea (in a concentration of about 0.1 to 3 M) is added to a buffer (pH 9 or more) such as the eluents (2) and (3) as mentioned above, the elution can be carried out very effectively.

This suitable second elution step can be carried out, for example, by eluting the HBs antigen-adsorbed silica with a mixture of 0.05 M sodium carbonate-sodium hydrogen carbonate buffer (pH 10.5)+1 M urea, by which HBs antigen can be recovered in a very high recovery rate without deterioration of HBs antigen in the biological and physical properties. This elution is usually carried out by shaking or stirring the mixture at a temperature of 0° to 40° C., preferably 4° to 35° C., for about 30 minutes to 3 hours. The eluent is used in an amount of 15 to 30 times by volume based on the volume of the HBs antigen-adsorbed silica. After the elution, the eluted mixture is centrifuged to separate the supernatant containing HBs antigen in a usual manner.

The adsorption chromatography with silica and the elution with a urea-added eluent as mentioned above have the following advantages.

(i) HBs antigen can be recovered in such a high rate as 95% or more from the starting HBs antigen-containing solution, that is, the purification can be extremely effectively carried out. [the recovery rate is measured by radioimmunoassay with AUSRIA-II, manufactured by Dainabbott, Japan]

(ii) The eluted solution has about ten times of specific activity: [HBs antigen protein content (μg/mol)/total protein content (mg/mol] as much as the amount of the starting solution, that is, the purification degree is so high.

(iii) The substance having a protease activity can almost completely be removed. Even when the eluted solution is kept at 4° C. for one month as it stands or after being regulated at pH 7.2, the antigenicity of HBs antigen is almost not decreased.

The elution in the presence of urea has various advantages as mentioned above and is further advantageous in the subsequent purification procedures. Since no surfactant such as deoxycholic acid is present in the elution step, any extra procedure for removing deoxycholic acid is required, and hence, the purification of HBs antigen is effectively done while keeping the high quality of the product.

In order to further highly purify the HBs antigen obtained by the adsorption chromatography with silica, the HBs antigen-containing eluate is regulated to about pH 6.5 to 8 with diluted acetic acid (about 10%), and then subjected to gel filtration. The gel filtration is preferably carried out after concentrating the HBs antigen-containing eluate until a concentration of HBs antigen of about 5 to 10 times, by using, for example, a hollow fiber ultrafilter, or the like. Carrier for the gel filtration includes a gel having a fractionation capacity of a critical molecular weight to be removed of $1 \times 10^5$ to $1 \times 10^6$. The HBs antigen is collected in the first peak fraction after initiation of elution which corresponds to the void volume, by which the contaminants having low molecular weight can effectively be removed. The carrier includes Sepharose CL-6B (manufactured by Pharmacia, Sweden), Cellulofine GC-700 (manufactured by Chisso, Japan), and any other commercially available carriers.

The gel filtration can be carried out by a conventional method, for instance, by passing the HBs antigen-containing solution purified by the above silica adsorption chromatography through a column packed with a gel which is equilibrated with a 0.14 M sodium chloride-added phosphate buffer (pH 7.2), passing through the above buffer, by which HBs antigen and contaminants are fractionated depending on the size of molecule thereof, and then taking out an HBs antigen-containing fraction. According to this procedure, the HBs antigen thus obtained shows an increased specific activity of about 3 to 10 times larger.

The HBs antigen thus purifed is preferably subjected to a further purification in a usual manner, such as sucrose density gradient ultracentrifugation or cesium chloride ultracentrifugation to give a highly purifed HBs antigen suitable for preparing the final HBV vaccine product. Preferably, the above further purification is carried out by adsorption chromatography with hydroxyapatite, by which the HBs antigen is more effectively purified to give the desired highly pure HBs antigen.

The adsorption chromatography with hydroxyapatite is carried out, for instance, by equilibrating a hydroxyapatite-packed column with a 0.1 M potassium phosphate buffer (pH 7.2), and passing through the column an HBs antigen-containing solution purified by the above gel filtration which is previously dialyzed against the above buffer, by which the HBs antigen is adsorbed thereon. The column is washed well with the buffer for equlibration as mentioned above, and then, HBs antigen is eluted with a 0.5 M potassium phosphate buffer (pH 7.2) to collect an HBs antigen-containing fraction. By the above procedure, the HBs antigen shows an increased specific activity of about 10 to 20 times larger.

After the purification procedure with hydroxyapatite as mentioned above, the HBs antigen is optionally subjected to dialysis, concentration and sucrose ultra-centrifugation to give an extremely highly pure HBs antigen.

According to the present invention, the desired highly purified HBs antigen suitable for the preparation of HBV vaccine can be obtained in such a high yield as 40% by weight or more from the starting materials, and hence, the present invention is industrially very useful for purification of HBs antigen.

The present invention is illustrated by the following Reference Example and Examples but should not be construed to be limited thereto.

REFERENCE EXAMPLE

In accordance with the method of Miyanohara et al. (cf. Japanese Patent First Publication No. 31799/1984), a transformed yeast being capable of producing HBs antigen is prepared and is cultured to produce HBs antigen, and the HBs antigen is separated and purified as follows.

(1) Preparation of HBV DNA (i) Preparation of virus DNA

A pooled blood plasma (700 ml) obtained from ten persons (subtype adr) who are positive in HBsAg and HBeAg is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (pH 7.5) of 10 mM Tris-HCl, 0.1 M NaCl and 1 mM EDTA. The solution is added to the top of a centrifugal tube containing 30% sucrose, which is centrifuged at 4° C., 39,000 r.p.m. for 4 hours. The resultant precipitates are re-dissolved in the same buffer as above.

The buffer solution is subjected to the reaction by HBV DNA polymerase by treating it in a mixture (500 μl) of 67 mM Tris-HCl (pH 7.5), 80 mM NH₄Cl, 25 mM MgCl₂, 0.5% (W/V %, hereinafter, the same) NP40 (tergitol, manufactured by Sigma Co.), 0.1% 2-mercaptoethanol, 330 μM dCTP (deoxycytidine triphosphate), dGTP (deoxyguanosine triphosphate), and dATP (deoxyadenosine triphosphate), 0.5 μM α-[$^{32}$P]dTTP (deoxythymidine triphosphate) at 37° C. for 30 minutes. To the reaction mixture is added dTTP in a final concentration of 330 μM, and the mixture is further reacted at 37° C. for 3 hours, and to the reaction mixture is added the same volume of 100 mM EDTA solution. By the above DNA polymerase reaction, single-stranded region of the HBV DNA is repaired to wholly double-strand to give a [$^{32}$P] labeled material. This material is added to the top of a centrifugal tube wherein 30%, 20% and 10% aqueous solutions of sucrose are layered in this order, and it is centrifuged at 4° C., 39,000 r.p.m. for 4.5 hours.

In order to digest the proteins strongly bonded to DNA, the precipitates obtained above are treated in a mixture (200 μl) of 1 mg/ml of pronase E (manufactured by Kaken Kagaku K.K.) and 0.2% aqueous sodium lauryl sulfate solution at 37° C. for 3 hours. The resulting DNA is extracted with phenol (200 μl) twice, and the resulting DNA-containing extract is washed with ether to remove phenol solvent to give a solution of HBV DNA. The DNA thus obtained has a specific radioactivity of $2.5 \times 10^6$ cpm/μg and can be used for digestion with restriction enzymes.

(ii) Cloning of HBV DNA

The double-stranded circular HBV DNA obtained above is cloned by using λ-phage Sharon 16A DNA as a vector and then is again cloned by using the known plasmid pACYC177 as a vector as follows.

(A) Cloning in the system of λ-phage Sharon 16A host-vector:

HBV DNA (20 ng) is treated with endonuclease Xho I in a mixture (20 μl) of 10 mM Tris-HCl (pH 7.4), 7 mM MgCl₂, 100 mM NaCl and 7 mM 2-mercaptoethanol at 37° C. for 2 hours. The resulting mixture is extracted with phenol (20 μl) and further with ether, and to the aqueous layer is added a double volume of cooled ethanol to precipitate DNA. The mixture is kept at −70° C. for one hour and then centrifuged at 10,000 r.p.m. for 5 minutes, and the precipitated DNA is recovered. The precipitates thus separated are dissolved in a mixture (5 μl) of 10 mM Tris-HCl (pH 7.4) and 1 mM EDTA. The HBV DNA and an equimolar amount of λ-phage Sharon 16A DNA (having one recognition site of Xho I) obtained by cleavage with endonuclease Xho I in the same manner as above are reacted with T4 DNA ligase [a mixture (10 μl) of 50 mM Tris-HCl (pH 7.4), 10 mM MgCl₂, 10 mM dithiothreitol, 100 μg/ml calf serum albumin, 0.5 mM ATP and 0.5 μl enzyme preparation (T4 ligase, manufactured by Takara Biomedicals, $1-5 \times 10^3$ unit/ml)] at 4° C. for 18 hours. The reaction mixture is extracted with phenol and ether and then subjected to precipitation with ethanol in the same manner as described above. The precipitates thus obtained are dissolved in a mixture (10 μl) of 10 mM Tris-HCl (pH 7.4) and 1 mM EDTA.

The thus annealed DNA is subjected to in vitro packaging operation to form λ-phage in the same manner as described in "Methods in Enzymclogy", 68, 299-309 and further plaques ($10^4$) are formed therefrom on an L-agar plate (23 cm×23 cm) by using *E. coli* DP50 SupF (cf. Blattner, F. R. et al, Science 196, 161, 1977) as an indicator. These plaques are subjected to plaque hybridization using $^{32}$P-labeled HBV DNA prepared above as a probe (cf. Science, 196, 180, 1977) in order to select plaques formed from the phage having HBV DNA, by which a plural of the desired phages are separated.

(B) Re-cloning by using plasmid pACYC177 as a vector:

From the phage having HBV DNA obtained in the above (A), a phage DNA is prepared by using *E. coli* DP50-SupF as a bacteria to be infected in the same manner as described in "Methods in Enzymology", 68, 245-378, 1979. The DNA thus obtained is digested with Xho I under the same conditions as described above for 2 hours, and the resulting reaction mixture is subjected to an electrophoresis with 0.75% agarose gel to isolate HBV DNA (3.2 kb). The HBV DNA is adsorbed onto DEAE (diethylaminoethyl cellulose) paper (manufactured by Toyo Roshi, Japan) in order to separate from the vector DNA and then eluted with 1 M NaCl aqueous solution to give an HBV DNA having Xho I terminals at both ends.

Separately, plasmid pACYC177 (cf. Chang, A.C.Y., Cohen, S. N.; J. Bacteriol., 134, 1141-1156, 1978) having a single Xho I cleavage site within kanamycin-resistant gene thereof is digested with Xho I, and the product is purified by phenol extraction, ether treatment and ethanol precipitation in the same manner as described above.

The thus obtained pACYC177 cleaved with Xho I is mixed with XhoI-terminal HBV DNA obtained above in a molar ratio of 1:5, and covalently joined by a T4 DNA ligasecatalyzed reaction for 18 hours as described above.

The reaction mixture (10 μl) is added to 0.1 ml of *E. coli*χ1776 [cf. R. III. Curtiss, et al, "Molecular cloning of recombinant DNA" eds. W. A. Scott and R. Werner, page 99, Academic Press (1977)] which is prepared by the procedure as described in M. V. Norgard, Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml) and is incubated at 37° C. overnight. The resulting colonies are applied onto both an agar plate containing kanamycin (20 μg/ml) and an agar plate containing ampicillin (20 μg/ml), and the colonies which grow only on the agar plate containing ampicillin is selected. From the colonies thus selected, a plasmid is prepared by the procedure as described by K. Matsubara (J. Virol., 16, 479, 1975). The plasmid thus obtained, i.e. the recombinant DNA of pACYC177-HBV DNA (which is designated "pHBV"), is treated with Xho I under the same conditions as described above to give total HBV DNA fragment (3.2 kb).

(2) Preparation of shuttle vectors pAM82

An EcoRI fragment of about 8,000 nucleotide pair (8 kb) containing a polypeptide (P60) gene of 60,000 dalton which constitutes the repressible acid phosphatase (RAP) (available from Yeast S288C gene bank; cf. Clarke, L. and Carbon, J., Cell, 9, 91-99, 1976) is inserted into the EcoRI site of known *E. coli* plasmid pBR322 to give a plasmid, which is used as the starting material.

To remove coding sequence of RAP, the starting plasmid is digested with a restriction enzyme Sal I and covalently joined again with T4 DNA ligase. The resulting plasmid pAT25 is deficient from the Sal I site to the acid phosphatase gene fragment 5.2 kb [said plasmid pAT 25 being a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof].

Into the EcoRI site of the above pAT 25 is inserted an EcoRI fragment (1.4 kb) containing ars 1 and Trp 1 gene which is prepared by treating a plasmid YRP 7 (cf. Struhl, K. et al, Proc. Natl. Acad. Sci. U.S.A., 76, 1035-1039, 1979) with EcoRI to give a plasmid pAT 26. Said ars 1-Trp 1 fragment has a single recognition site of a restriction enzyme Hind III within the Trp 1 gene.

Into the Hind III site of the above pAT 26 is inserted a Hind III fragment containing a Leu 2 and 2 μori which is prepared by treating a plasmid pSLE 1 (cf. Tohe, A. et al, J. Bacteriol., 141, 413-416, 1980) with Hind III to give a shuttle vector pAT 77. The pAT 77 carried on *Saccharomyces cerevisiae* (i.e. Saccharomyces cerevisiae AH 22/pAT 77) has been deposited at Fermentation Research Institute, Agency of Industrial Science and Technology, Japan under Budapest Treaty as "FERM BP-324".

The pAT 77 thus obtained (1 μg) is cleaved with Sal I and then is treated with an exonuclease BAL 31 (0.1 U) in a solution (50 μl) of 20 mM Tris-HCl (pH 8.2), 12 mM $CaCl_2$, 12 mM $MgCl_2$, 0.2 M NaCl and 1 mM EDTA for 30 seconds to one minute. The reaction mixture is subjected to phenol extraction and ethanol precipitation in the same manner as described above. The resulting precipitates are mixed with Xho I linker (1 pmol) and joined by T4 DNA ligase under the same conditions as described above for 12 hours.

*E. coli*χ1776 is transformed with the above reaction mixture by the procedure as described in R. III. Curtiss et al, "Molecular cloning of recombinant DNA" eds. W. A. Scott and R. Werner, page 99, Academic Press (1977), and from the resulting transformants, plasmid DNAs are prepared by the procedure as described by K. Matsubara (j. Virol., 16, 479, 1975). According to Maxam-Gilbert method (cf. Maxam, A. & Gilbert, W.; Pro. Natl. Acad. Sci., 74, 560-564), the nucleotide sequence of the resulting DNAs is determined, and further, the region of the acid phosphatase gene deleted with BAL 31 is determined. Among these DNAs, the desired plasmids pAM 82 is selected and isolated.

Designating "A" in the codon ATG encoding the first amino acid (methionine) of the product P60 of the phosphatase structural gene as "+1", in the shuttle vector pAM 82, the region till −33 is deleted. The pAM 82 carried on *Saccharomyces cerevisiae* (i.e. *Saccharomyces cerevisiae* AH 22/pAM 82) has been deposited at Fermentation Research Institute, Agency of Industrial Science and Technology, Japan under Budapest Treaty as "FERM BP-313".

(3) Preparation of HBsAg gene-expression plasmids

HBV DNA obtained by treating a plasmid pHBV with Xho I is recombined with Xho I cleaved shuttle vector pAM 82 in the molar ratio of 5:1 by T4 DNA ligase under the same conditions as described above.

E. coli$\chi$1776 is transformed with the reaction mixture and a plasmid DNA is prepared from the resulting ampicillin-resistant transformant. The DNA thus prepared is analyzed with various restriction enzymes, such as Xho I, Xba I and Hind III, and thereby, insertion of HBV DNA into the vectors and direction thereof are determined.

The thus obtained HBsAg gene-expression plasmid (designated pAH 203) has HBs gene and HBc gene in this order downstream the phosphatase promoter, which is an HBs Ag-expressing plasmid.

(4) Preparation of transformed yeast

The starting yeast is *Saccharomyces cerevisiae* AH22 [a, leu2, his4, canl (Cir$^+$)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2% glucose, and the mixture is incubated at 30° C. overnight, and thereafter, the cells are collected by centrifugation. The cells thus collected are washed with sterilized water (20 ml), suspended in a solution (5 ml) of 1.2 M sorbitol and 100 $\mu$g/ml zymolyase-60,000 (manufactured by Seikagaku Kogyo K. K., Japan), and the suspension is allowed to stand at 30° C. for 30 minutes to give spheroplast. The spheroplast thus prepared is washed with 1.2 M sorbitol solution three times, and then suspended in a solution (0.6 ml) of 2 M sorbitol, 10 mM CaCl$_2$ and 10 mM Tris-HCl (pH 7.5). The suspension thus prepared is divided into a small test tube in a volume of 60 $\mu$l. To the suspension is added the solution of the recombinant plasmid pAH 203 (30 $\mu$l) prepared in the above (3). After mixing well, 0.1 M CaCl$_2$ (3 $\mu$l) is added thereto in a final concentration of 10 mM CaCl$_2$, and the mixture is allowed to stand at room temperature for 5 to 10 minutes. To the resulting mixture is added each 1 ml of a solution of 20% polyethylene glycol 4,000, 10 mM CaCl$_2$ and 10 mM Tris-HCl (pH 7.5), and the mixture is allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 $\mu$g/ml histidine and 3% agar, which is kept at a constant temperature of 45° C. After gently mixing, the mixture is added in a layer onto a plate of minimal medium containing 1.2 M sorbitol which is previously prepared and consists of 0.7% yeast nitrogen base amino acid, 2% glucose, 20 $\mu$g/ml histidine and 2% agar and is set thereon. The plate is incubated at 30° C. to give a colonie of a leucine-nonrequiring yeast. The colonie is incubated in a BurkHolder minimal medium supplemented with histidine (20 $\mu$g/ml) [cf. Tohe, A, et al; J. Bachterol., 113, 727–738, 1973] to give the desired transformed yeast: *Saccharomyces cerevisiae* pAH 203.

(5) Production of HBsAg with the transformed yeast

The transformed yeast obtained in the above (4) is inoculated into BurkHolder minimal medium (10 ml) supplemented with histidine (20 $\mu$g/ml) and incubated at 30° C. The resulting culture is further inoculated into BurkHolder minimal medium (10 liters) supplemented with histidine (20 $\mu$g/ml) and incubated with stirring at 30° C. for 48 hours. The cells in logarithmic growth phase are collected by centifugation, suspended in a minimal medium (10 liters) containing no phosphate (which is prepared by replacing KH$_2$PO$_4$ in BurkHolder minimal medium with KCl, followed by supplementing with 20 $\mu$g/ml histidine) in a cell concentration of about 4$\times$10$^6$ cells/ml. After incubating at 30° C. for about 24 hours, the culture medium is centrifuged at 4,000 r.p.m. for 10 minutes to collect the cells (about 120 g).

Example 1

To the cells (about 1 kg) obtained by repeating the procedure as in the above Reference Example is added 0.14 M sodium chloride-added 0.1 M phosphate buffer (pH 7.2) (5 liters), and the mixture is treated with a Manton-Gaulin fracturing machine under a pressure of 600 to 700 kg/cm$^2$ to fracture the cells. The fractured cells are centrifuged to remove course pieces of the fractured cells to give a staring material (5 liters) containing HBs antigen (8.0 mg).

The starting material is subjected to the first elution step as follows.

To the starting material (5 liters) is added fine particles of silicic anhydride (Mizukasil P-526, manufactured by Mizusawa Kagaku K. K., Japan) (0.15 kg), and the mixture is vigorously stirred at 10° C. for 4 hours, by which HBs antigen is adsorbed onto the silica. The mixture is centrifuged at 3,500 r.p.m. for 10 minutes, and the supernatant is removed. To the resulting precipitates is added a 0.14 sodium chloride-added phosphate buffer (pH 7.2) (5 liters), and the mixture is stirred at 10° C. for 3 hours, and centrifuged at 3,500 r.p.m. for 10 minutes, and the supernatant is removed. To the resulting precipitates of HBs antigen-adsorbed silica is again added a 0.14 sodium chloride-added phosphate buffer (pH 7.2) (5 liters), and the mixture is again subjected to the above procedure.

After finishing the above first elution step, the HBs antigen-adsorbed silica is subjected to the second elution step.

That is, to the HBs antigen-adsorbed silica is added a mixture (2.5 liters) of a 0.05 M sodium carbonatesodium hydrogen carbonate buffer (pH 10.5) and urea (concentration: 1 M/liter), and the mixture is vigorously stirred at 37° C. for 2 hours. Thereafter, the mixture is centrifuged at 3,500 r.p.m. for 10 minutes, and then a supernatant (2.5 liters) containing HBs antigen is obtained.

To the HBs antigen-containing solution is gradually added 10% aqueous acetic acid solution to regulate pH 7.2, and the solution is concentrated until about 300 ml with a hollow fiber ultrafilter (manufactured by Asahi Chemical, Japan). The solution is subjected to a gel filtration by passing through a column packed with sepharose CL-6B gel (manufactured by Pharmacia) (gel volume: about 10 liters) which is previously equlibrated with a 0.05 M potassium chloride-added 0.1 M potassium phosphate buffer (pH 7.2), and then eluting with the same buffer as above. With analyzing by reverse passive hemagglutination using an anti-HBs antibody, a fraction containing HBs antigen is pooled to give an HBs antigen solution (1.8 liters) purified by gel filtration.

This HBs antigen solution purified by gel filtration is passed through a column packed with a hydroxyapatite (Hydroxyapatite-Spheroidal, manufactured by BDH Chemical) (gel volume: 800 ml) which is equilibrated with a 0.05 M potassium chloride-added 0.1 M potassium phosphate buffer (pH 7.2), by which HBs antigen is adsorbed on the gel. After the column is washed well with the same buffer as above, a 0.05 M potassium chloride-added 0.5 M potassium phosphate buffer is passed therethrough to elute HBs antigen to give a purified HBs antigen-containing solution (HTP elution fraction). The yield of HBs antigen, the degree of purification and the content of substance having protease activity in each step are shown in Table 1.

According to the present invention, there can be obtained a highly pure HBs antigen product having less contaminant and showing a single band of HBs antigen (by the analysis in accordance with SDS-polyacrylamide gel electrophoresis) when subjected to a sucrose step ultracentrifugation.

TABLE 1

| Steps | Recovery[1] rate (%) | Degree[2] of purification | Content of sub-[3] stance having protease activity ($\mu$g/ml) |
|---|---|---|---|
| Starting material | 100 | 1 | More than 800 |
| Eluate in second elution step with silica | 91 | 9.8 | Less than 50 |
| Purified fraction in gel filtration | 77 | 34.3 | Less than 50 |
| HTP elution fraction | 46 | 617 | Less than 50 |

[Note]
[1] It was measured by a radioimmunoassay method using AUSRIA-II (manufactured by Dainabbott, Japan), wherein a purified product of a human-origin HBs antigen was used as a reference.
[2] It means a relative specific activity of each fraction when the specific activity [HBs antigen content ($\mu$g/ml)/total protein content (mg/ml)] of the starting material was counted as 1.
[3] It was measured by using Protease Substrate Gel Tablets (manufactured by Bio Rad) and calculated based on a calibration curve in trypsin ("tripsin 1:250" manufactured by DIFCO, critical amount for measurement: 50 $\mu$g/ml trypsin).

What is claimed is:

1. A method for the purification of HBs antigen produced by a recombinant organism being capable of producing HBs antigen which is prepared by means of DNA recombination technique, which comprises subjecting an HBs antigen-containing material produced by a recombinant organism to an adsorption chromatograph with a fine powder or particle silica of not more than 10 $\mu$, subjecting the resultant HBs antigen-adsorbed silica to first elution step with a buffer having pH 5 to 9 to remove contaminants and then to second elution step with a buffer having a pH 9 or more which is incorporated with 0.1 to 3 M urea, followed by subjecting to an adsorption chromatography with a hydroxyapatite.

2. The method according to claim 1, wherein the starting HBs antigen-containing material is a crude extract of HBs antigen which is prepared by fracturing recombinant cells by ultrasonic fracture, glass beads fracture, Manton-Gaulin fracture, or fracturing with a detergent.

3. A method for the purification of HBs antigen produced by a recombinant organism being capable of producing HBs antigen which is prepared by means of DNA recombination technique, which comprises subjecting an HBs antigen-containing material produced by a recombinant organism to an adsorption chromatography with a fine powder or particle silica of not more than 10 $\mu$, subjecting the resultant HBs antigen-adsorbed silica to first elution step with a buffer having pH 5 to 9 to remove contaminants and then to second elution step with a buffer having a pH 9 or more which is incorporated with 0.1 to 3 M urea, subjecting the resultant HBs antigen-containing eluate to a gel filtration, followed by subjecting to an adsorption chromatography with a hydroxyapatite.

* * * * *